US009486333B2

(12) United States Patent
Wang et al.

(10) Patent No.: US 9,486,333 B2
(45) Date of Patent: Nov. 8, 2016

(54) PROSTHETIC SOCKET APPARATUS AND SYSTEMS

(71) Applicant: Florida State University Research Foundation, Inc., Tallahassee, FL (US)

(72) Inventors: Ben Wang, Atlanta, GA (US); Chun Zhang, Marietta, GA (US); Changchun Zeng, Tallahassee, FL (US); Leslie David Kramer, Longwood, FL (US); Arlene Gillis, Tampa, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/864,675

(22) Filed: Apr. 17, 2013

(65) Prior Publication Data

US 2013/0274896 A1 Oct. 17, 2013

Related U.S. Application Data

(60) Provisional application No. 61/625,308, filed on Apr. 17, 2012.

(51) Int. Cl.
*A61F 2/78* (2006.01)
*A61F 7/00* (2006.01)
*A61F 2/76* (2006.01)

(52) U.S. Cl.
CPC ............... *A61F 2/7812* (2013.01); *A61F 7/00* (2013.01); *A61F 7/007* (2013.01); *A61F 2002/7665* (2013.01); *A61F 2002/7806* (2013.01); *A61F 2002/7818* (2013.01); *A61F 2007/0051* (2013.01); *A61F 2007/0075* (2013.01); *A61F 2007/0082* (2013.01); *A61F 2007/0086* (2013.01)

(58) Field of Classification Search
CPC ... A61F 2007/0051; A61F 7/00; A61F 7/007
USPC ....................................... 623/32–37
See application file for complete search history.

(56) References Cited

U.S. PATENT DOCUMENTS

| 4,869,250 | A | * | 9/1989 | Bitterly .................. 607/107 |
| 6,123,716 | A | * | 9/2000 | Augustine et al. ............ 607/104 |
| 2002/0156509 | A1 | * | 10/2002 | Cheung ........................ 607/96 |
| 2003/0157342 | A1 | * | 8/2003 | Myers et al. ................. 428/447 |
| 2005/0101693 | A1 | * | 5/2005 | Arbogast et al. ............. 523/122 |
| 2005/0125078 | A1 | * | 6/2005 | Br. Janusson et al. ......... 623/36 |

(Continued)

OTHER PUBLICATIONS

Smart Solutions from Auxetic Materials. Professor Andy Alderson of the University of Bolton. Med-Tech Innovation, Sep. 27, 2011. www.med-techinnovation.com/Articles/articles/article/20 Accessed May 14, 2014.*

(Continued)

*Primary Examiner* — Marcia Watkins
(74) *Attorney, Agent, or Firm* — Sutherland Asbill & Brennan LLP

(57) ABSTRACT

A prosthetic sock for a patient to wear over a residual limb is provided. The prosthetic sock includes an inner layer configured to fit over at least a portion of the residual limb of the patient. A foam layer is disposed on an outer surface of the inner layer. The foam layer compensates for changes in shape or volume of the residual limb within the prosthetic sock by changing shape in a manner effective to maintain a secure fit between the residual limb and a prosthetic socket of a prosthetic limb.

20 Claims, 5 Drawing Sheets

(56) References Cited

U.S. PATENT DOCUMENTS

| | | | | |
|---|---|---|---|---|
| 2006/0207931 | A1* | 9/2006 | Liang et al. | 210/500.21 |
| 2008/0141681 | A1* | 6/2008 | Arnold | A41D 13/005 62/3.5 |
| 2008/0188948 | A1* | 8/2008 | Flatt | 623/36 |
| 2010/0274364 | A1* | 10/2010 | Pacanowsky et al. | 623/36 |
| 2010/0318195 | A1* | 12/2010 | Kettwig et al. | 623/36 |
| 2013/0079893 | A1* | 3/2013 | Allemand | 623/36 |

OTHER PUBLICATIONS

Bauer, Siegfried et al., "Ferroelectrets: Soft Electroactive Foams for Transducers," Feb. 2004, Physics Today, American Institute of Physics, S-0031-9228-0402-010-1, http://www.physicstoday.org.

Board, W. J. et al., "A comparison of trans-tibial amputee suction and vacuum socket conditions," Prosthetics and Orthotics International, 2001, 25, 202-209.

Chein, Reiyu et al., "Performances of thermoelectric cooler integrated with microchannel heat sinks," International Journal of Refrigeration 28 (2005) 828-839.

Evans, K. E. et al., "Microporous materials with negative Poisson's ratios: II. Mechanisms and interpretation," J. Phys. D: Appl. Phys. 22 (1989) 1883-1887.

Hachisuka, Kenji et al., "Moisture Permeability of the Total Surface Bearing Prosthetic Socket with a Silicone Liner: Is it Superior to the Patella-Tendon Bearing Prosthetic Socket?" The UOEH Association of Health Sciences, J UOEH 23 (3): 225-232 (2001).

Han, Kerang et al., "Flow modeling and simulation of SCRIMP for composites manufacturing," Composites: Part A 31 (2000) 79-86.

Klute, G. K. et al., "The thermal conductivity of prosthetic sockets and liners," Prosthetics and Orthotics International, Sep. 2007; 31(3): 292-299.

Klute, Glenn K. et al., "Prosthetic liners for lower limb amputees: A review of the literature," Prosthetics and Orthotics International, Jun. 2010, 34(2): 146-153.

Lee, Haeshin et al., "A reversible wet/dry adhesive inspired by mussels and geckos," Letters, vol. 448, Jul. 19, 2008, doi:10.1038/nature05968.

Lee, Jongho et al., "Gecko-Inspired Combined Lamellar and Nanofibrillar Array for Adhesion on Nonplanar Surface," Langmuir 2009, 25 (21), 12449-12453, Published on Web Oct. 2, 2009, DOI: 10.1021/la9029672.

Luo, J. et al., "Optimum tooling design for resin transfer molding with virtual manufacturing and artificial intelligence," Composites: Part A 32 (2001) 877-888.

Mondal, S., "Phase change materials for smart textiles—An overview," Applied Thermal Engineering 28 (2008) 1536-1550.

Nielsen, Caroline C., "A Survey of Amputees: Functional level and life Satisfaction, Information Needs, and the Prosthetist's Role," JPO 1991, vol. 3, No. 3, p. 125.

Siivola, J. et al., Technical note, "ETMF-polymer transducer as a detector of respiration in humans," Med. & Biol. Eng. & Comput., 1993, 31, 634-635.

Wegner, Michael et al., "Microstorms in Cellular Polymers: A Route to Soft Piezoelectric Transducer Materials with Engineered Macroscopic Dipoles," ChemPhysChem 2005, 6, 1014-1025, DOI: 10.1002/cphc.200400517.

Zeng, Changchun et al., "Morphology and tensile properties of PMMA carbon nanotubes nanocomposites and nanocomposites foams," Composites Science and Technology 82 (2013) 29-37.

Zeng, Changchun et al., "Synthesis and processing of PMMA carbon nanotube nanocomposite foams," Polymer 51 (2010) 655-664.

Limb Loss Statistics, http://www.amputee-coalition.org/limb-loss-resource-center/resources-by-topic/limb-loss-statistics/limb-loss-statistics/, 5 pages, printed Nov. 11, 2015.

Board et al., "A comparison of trans-tibial amputee suction and vacuum socket conditions," Prosthetics and Orthotics International, 25 pp. 202-209 (2001).

Fernie et al., "Volume fluctuations in the residual limbs of lower limb amputees," Archives of Physical Medicine and Rehabilitation, 63 pp. 162-165 (1982).

Nielsen, "A survey of amputees: functional level and life satisfaction, information needs, and the prosthetist's role," Journal of Prosthetics and Orthotics, 3(3) pp. 125-129 (1993).

Klute et al., "The thermal conductivity of prosthetic sockets and liners," Prosthetics and Orthotics International, 31(3) pp. 292-299 (2007).

Ghoseiri et al., "Prevalence of heat and perspiration discomfort inside prostheses: Literature Review," Journal of Rehabilitation Research and Development, 51(6) pp. 855-868 (2014).

* cited by examiner

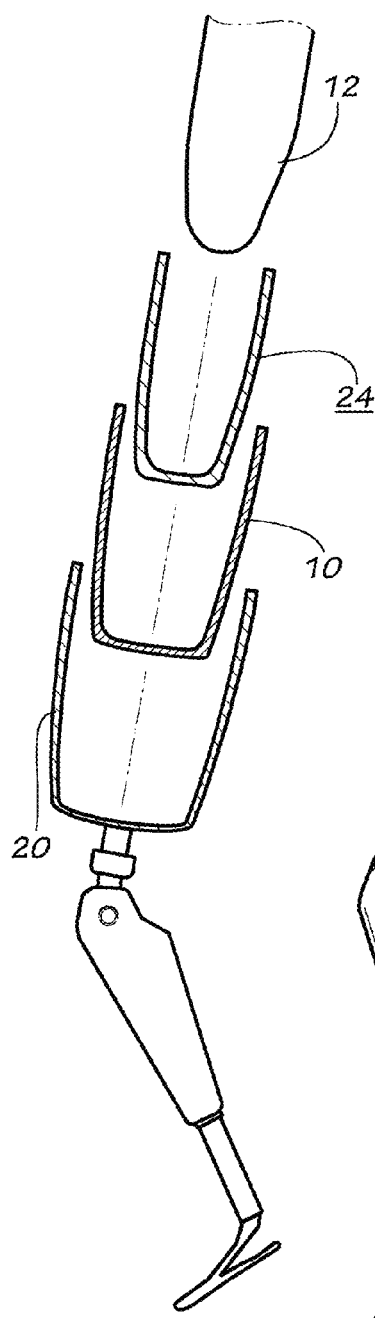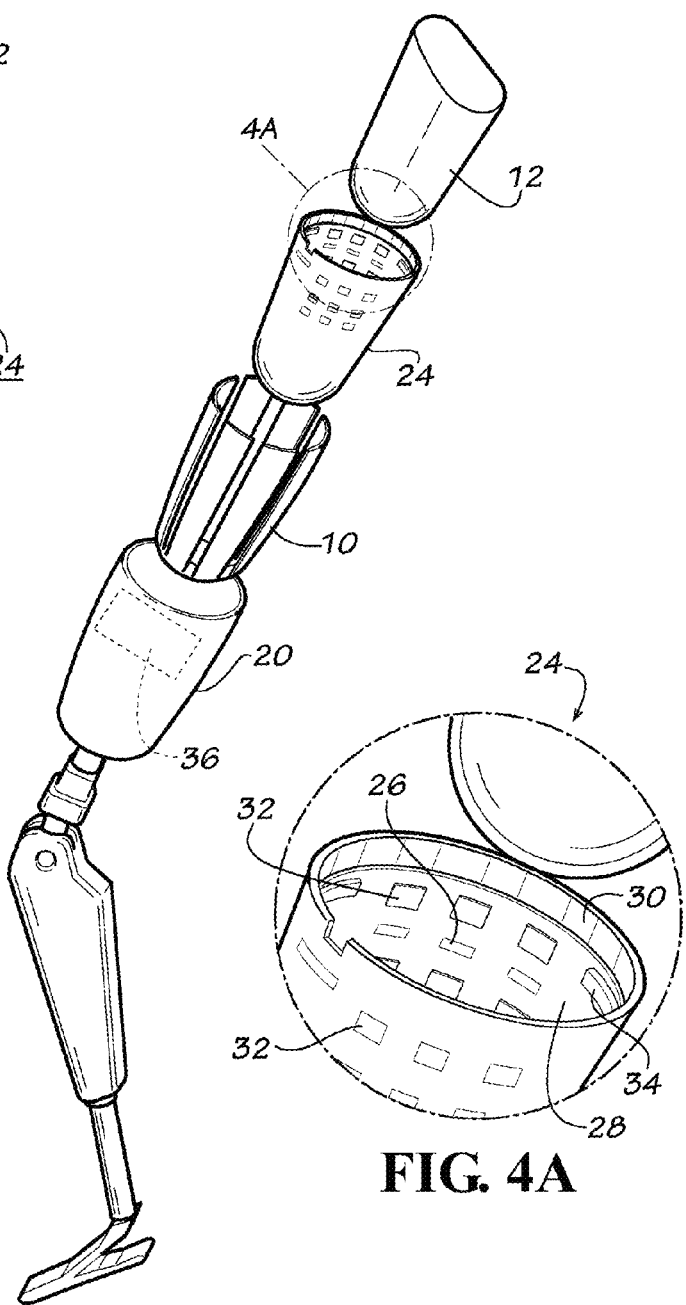
FIG. 3    FIG. 4    FIG. 4A

PROSTHETIC SOCKET APPARATUS AND SYSTEMS

CROSS REFERENCE TO RELATED APPLICATIONS

This application claims priority to U.S. Provisional Patent Application No. 61/625,308 filed on Apr. 17, 2012, the disclosure of which is incorporated in full herein by reference.

TECHNICAL FIELD

The present disclosure is generally in the field of prosthetic medical devices for amputees, including but not limited to prosthetic sockets.

BACKGROUND

In the past decade, significant advances have been made in the area of prosthetics. Many of the advanced commercialized prostheses have been designed and manufactured using new and emerging technologies including microprocessor knees (C-leg) and bionic ankles (IWalk). These new prostheses have played key roles in improving the prosthetic patients' quality of life. However, many surveys still indicate that amputees are not satisfied with their prostheses due to discomfort and adverse effects on their skin as a result of poor fit, elevated temperatures and moisture accumulation within the prosthetic socket. Recently, efforts have been made to develop various liner materials and components/mechanisms to address these issues. However, most efforts have focused on developing components/devices to enhance individual functions. Their effectiveness has been limited due to significant weight addition and lack of integration of these devices into a holistic socket system.

Conventional prosthetic socket designs suffer from a number of deficiencies. For example, many amputees experience daily volume changes in their residual limbs which a conventional socket design cannot accommodate. These volume changes affect the fit of the socket and the quality of an amputee's life. This is particularly important in the design of above-knee sockets, since the transfemoral amputee experiences the largest anatomical volume fluctuation of any limb deficiency. While socks designed for the residual limb may be added or removed to ameliorate the problem, even the most seasoned amputees and practitioners have difficulty determining suitable sock ply adjustments. This volume change leads to a poor fit of the prosthetic and may cause instability of the residuum, resulting in pistoning of the limb within the socket which often leads to the formation of sores on the amputee's skin. Additionally, elevated temperatures inside a conventional prosthetic socket may also be detrimental to the skin, causing heat rash and maceration, which may further lead to tissue breakdown.

Thus, there is a need for new prosthetic sockets and socket systems to address these and other deficiencies of conventional prosthetic sockets.

SUMMARY

In one aspect, a prosthetic sock for a patient to wear over a residual limb is provided. The prosthetic sock includes an inner layer configured to fit over at least a portion of the residual limb of the patient. A foam layer is disposed on an outer surface of the inner layer. The foam layer compensates for changes in shape or volume of the residual limb within the prosthetic sock by changing shape in a manner effective to maintain a secure fit between the residual limb and a prosthetic socket of a prosthetic limb.

In another aspect, a system for securing a residual limb in a prosthetic socket of a prosthetic limb is provided. The system includes a prosthetic sock to be worn over the residual limb of a patient and a prosthetic socket for receiving the residual limb with the prosthetic sock thereon. The prosthetic sock compensates for shape or volume changes in the residual limb by changing shape to maintain a secure fit between the residual limb and the prosthetic socket.

In a further aspect, a system for managing a prosthetic limb worn by a patient in provided. The system includes an electronics liner for disposition over a residual limb of a patient. A prosthetic sock may then be worn over the electronics liner and the residual limb. The prosthetic sock is configured to change shape in a manner effective to maintain a secure fit of the residual limb in a prosthetic socket of a prosthetic limb. The system also includes a prosthetic socket for receiving the prosthetic sock, the electronics liner, and the residual limb.

Additional aspects will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

These and other features, aspects, and advantages of the present invention will become better understood when the following detailed description is read with reference to the accompanying drawings.

FIG. 3 is a cross-sectional exploded perspective view of the residual limb, electronics liner, foam liner, and prosthetic socket, in accordance with embodiments of the present disclosure.

FIG. 4 is a cross-sectional perspective view of the view of FIG. 3, showing the integrated electronic systems, in accordance with embodiments of the present disclosure.

FIG. 4A is a perspective close-up view of the integrated electronic systems of the view of FIG. 4, in accordance with embodiments of the present disclosure.

Corresponding reference characters indicate corresponding parts throughout the several Figures. The exemplifications set out herein illustrate embodiments of the invention, sometimes in one form, and such exemplification should not be construed as limiting the scope of the claimed invention in any manner.

DETAILED DESCRIPTION

In the following description, numerous specific details are given to provide a thorough understanding of embodiments. The embodiments can be practiced without one or more of the specific details, or with other components, materials, etc. In other instances, well-known structures, materials, or operations are not shown or described in detail to avoid obscuring aspects of the embodiments.

Reference throughout this specification to "one embodiment," "an embodiment," or "embodiments" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Prosthetic sockets providing improved patient comfort and functionality have been developed. In embodiments, the sockets incorporate one or more of several technologies to improve patient comfort: (1) volume/shape change management; (2) pistoning control and lesion avoidance; (3) temperature and sweat control; and (4) sensor integration across multiple components. In one embodiment, volume/shape change management is realized with advanced materials that sense and respond to external stimuli, such as pressure changes due to either volume changes as a result of residual limb swelling or muscle tissue shape changes during a gait cycle. Pistoning control and skin breakdown prevention may be realized via an interface material that may be embedded with nanoparticles. In one embodiment, temperature and sweat control are achieved by solid state active cooling using an array of miniature thermoelectric devices in combination with nanomaterials or phase change materials or both. In an embodiment, lightweight piezoelectric nanofoam pressure sensors and printed electronic temperature and moisture sensors fully embedded in liners provide the patient with an early warning of adverse situations, such as abnormal pressure suggesting improper gait or pistoning, and allow the practitioner to remotely collect real-time data for analysis.

The terms "patient" and "amputee" are used interchangeably to refer to the human (or other animal) that has had a limb, particularly a leg, partially amputated, above or below the joint (e.g., the knee). In a particular embodiment, the patient is an above-the-knee amputee.

Volume Change Management

Figure 1:
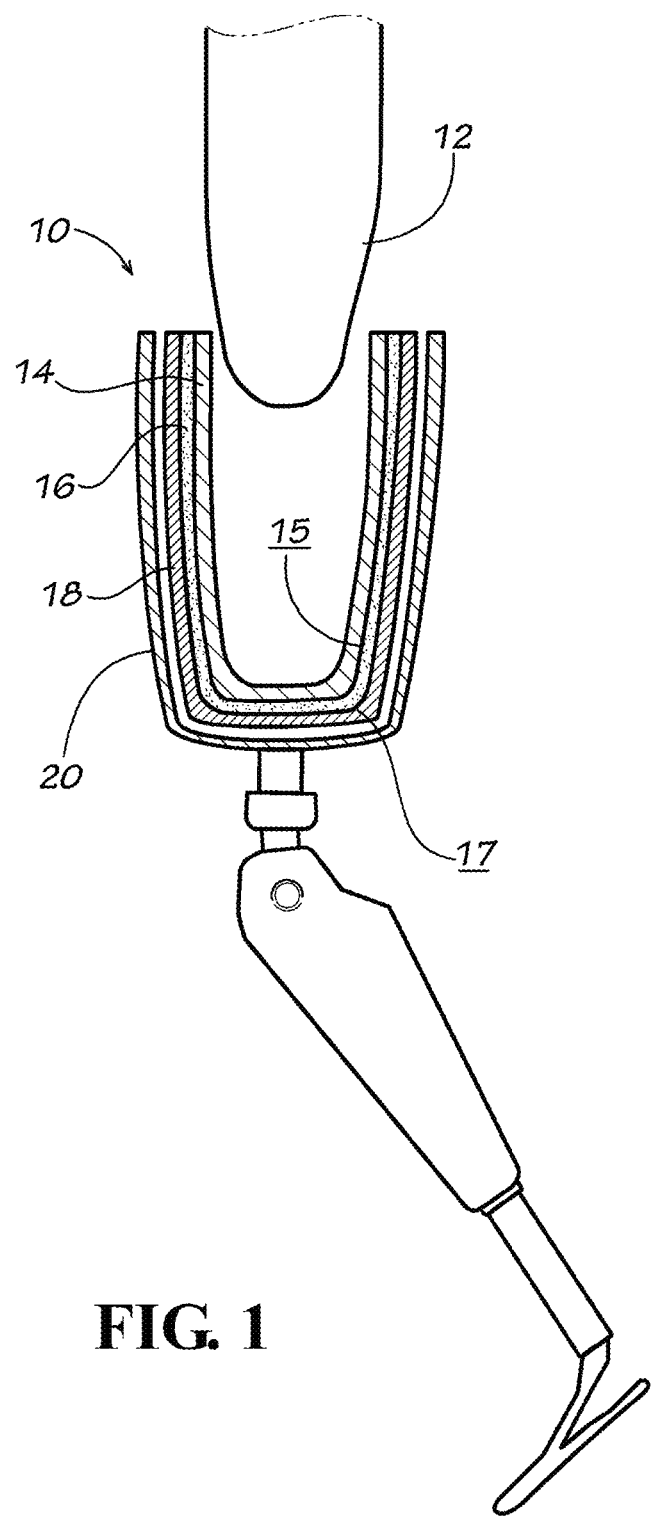
FIG. 1 is a cross-sectional perspective view of a prosthetic socket assembly, in accordance with embodiments of the present disclosure. Any spaces shown between the layers are for illustrative purposes only and would not be present in embodiments of this disclosure.

Referring now to the drawings, and more particularly to FIG. 1, a prosthetic sock 10 is shown for a patient to wear on a residual limb 12. The prosthetic sock 10 includes an inner layer 14 that is configured to fit over at least a portion of the residual limb 12. A foam layer 16 is disposed on an outer surface 15 of the inner layer 14. In some embodiments, the foam layer 16 is attached to the outer surface 15 of the inner layer 14 by an adhesive. The foam layer 16 is configured to respond to and compensate for changes in shape or volume of the residual limb 12 within the prosthetic sock 10. The foam layer 16, located between the stump and the socket, changes shape or volume in a manner effective to maintain a secure fit between the residual limb 12 and a prosthetic socket 20 of a prosthetic limb. In other embodiments, the foam layer 16 is configured to respond to and compensate for changes in the shape of a residual limb 12 within a prosthetic sock 10.

In a typical embodiment, the volume of a residual limb 12 changes between plus or minus about 15% on a regular basis, leading to periodic changes in the fit of the prosthetic socket 20 on the residual limb 12. In some embodiments, the foam layer 14 of the prosthetic sock 10 is configured to change shape to one or more second shapes, each of which substantially matches the shape of the residual limb 12. In some embodiments, the foam layer 16 has an initial volume and the foam layer 16 is configured to change to a second volume by an amount in the range of from about −100% to about +300% of the initial volume of the foam layer 16. In still other embodiments, the foam layer 16 is configured to change to a second volume by an amount in the range from about −50% to about +150%, from about −25% to about +100%, from about −25% to about +50%, from about −10% to about +25%, or from about −15% to about +15% of the initial volume of the foam layer 16.

In some embodiments, the foam layer 16 is a biocompatible foam. In some embodiments, the foam layer 16 comprises a polyurethane foam material, including but not limited to super-cushioning polyurethanes, Poron urethanes, viscoelastic foams, polyester foams, polyethers, polytetrafluoroethylene (PTFE) polymers, and the like.

Auxetic Foams

In a preferred embodiment, the foam layer comprises an auxetic foam. In some embodiments, the foam layer comprises an auxetic foam that is fabricated from one or more polyurethane foam materials. To convert a polyurethane foam into an auxetic foam, the polyurethane foam is compressed to force the cell ribs of the polymer to buckle. The compressed foam is then heated to the softening temperature to preserve the new configuration. The foams are then cooled to room temperature to freeze the re-entrant structures. The softening temperature, heating time, and compression ratio vary among the polyurethane foams and the resulting auxetic foams and are processing factors to be considered when fabricating auxetic foams with desirable properties. In other embodiments, the auxetic foam is a commercially available auxetic foam.

Figure 2:
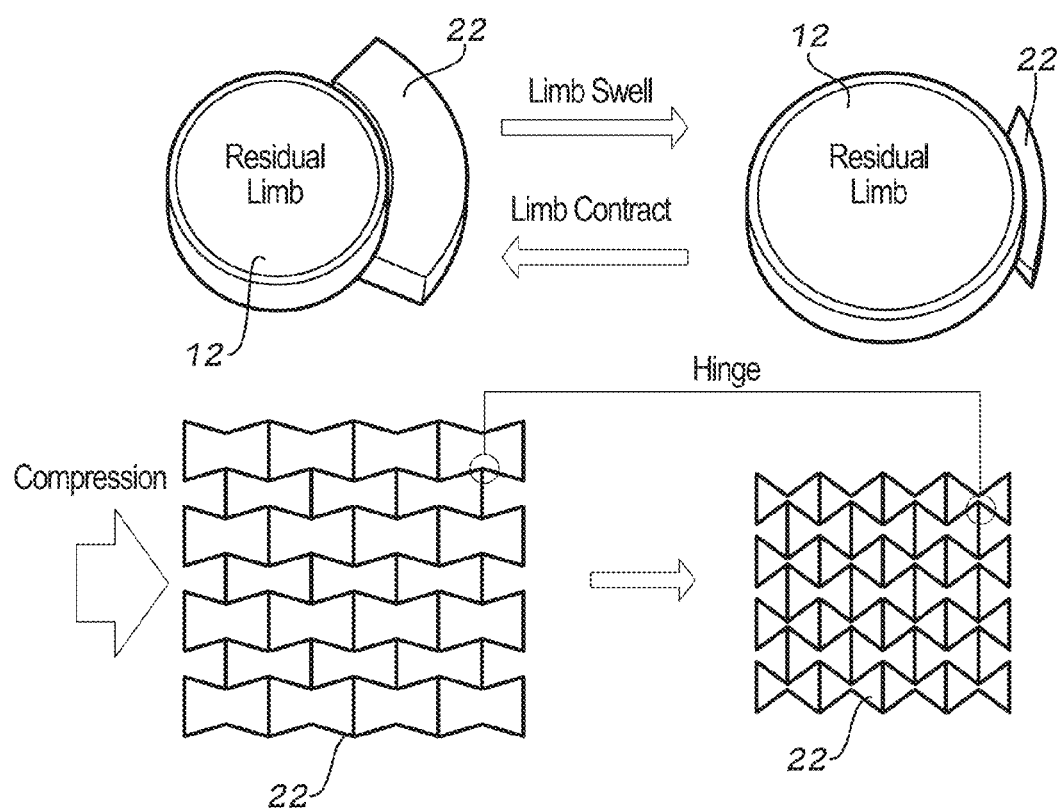
FIG. 2 is a schematic view of how auxetic foams accommodate socket volume changes from limb swell and contraction, in accordance with embodiments of the present disclosure. The bottom portion of FIG. 2 is a schematic view of the auxetic foam structure and working principle, in accordance with embodiments of the present disclosure.

Auxetic foam may be particularly suitable for volume compensation. FIG. 2 shows an example of the auxetic structure and how the volume changes in response to external forces. As the residual limb 12 swells, the auxetic foam 22 shrinks in all directions making room to accommodate the residual limb 12 swelling, unlike other foam materials that typically expand sideways providing no space for the swollen stump. When the residual limb 12 contracts, the auxetic foam 22 expands in all directions, filling the extra space to maintain a comfortable fit. This provides a self-regulating mechanism to accommodate volume changes in all directions within the rigid socket shell.

The bottom portion of FIG. 2 is a schematic view of the auxetic foam 22 hinged structure and working principle. The auxetic foam 22 is depicted as a network of linked inverse trapezoids. Under compression (limb swell), the trapezoids shrink. The linked trapezoids (via the hinge in the figure) leads to the overall shrinkage of the auxetic foam 22.

Turning back to FIG. 1, in some embodiments, the prosthetic sock also includes an outer layer 18 located along the outer surface 17 of the foam layer 16. In some embodiments, the outer layer 18 material is connected to the foam layer 16 by an adhesive, thermal bond, or other bonding or fastening methods. In some embodiments, the outer layer 18 is a sock-like material. In other embodiments, the outer layer may include a woven or a non-woven material.

In embodiments, the inner layer 14 is a sock-like material that makes up the inner surface of the foam layer 16. In some embodiments, the inner layer 14 may comprise a woven or a non-woven material.

In some embodiments, the prosthetic socket 20 may further include a silicon rubber liner configured to make direct contact with the skin surface of the residual limb 12. In operation, the prosthetic socket 20 may be partly secured to the residual limb 12 under reduced pressure relative to atmospheric pressure. In some embodiments, the top 3 inches, the top 2 inches, or the top inch of the silicon rubber liner is in direct contact with the user's leg.

In some embodiments, the residual limb 12 may comprise the remaining leg from an above-the-knee amputation. In other embodiments, the residual limb 12 may comprise the remaining leg from a below-the-knee amputation. In still other embodiments, the residual limb 12 may comprise another post-amputation appendage. In particular embodiments, the residual limb 12 may comprise the remaining arm from an above-the-elbow amputation. In other embodiments, the residual limb 12 may comprise the remaining arm from a below-the-elbow amputation.

Pistoning Control and Lesion Management

As discussed above, a typical amputee's residual limb can swell or shrink in volume depending on hydration, humidity, barometric pressure, edema, diet, and other factors. Thus, the instantaneous fit between the inner surface of a conventional socket and the liner changes during the day. These volume changes allow relative movements between the liner internal surface and the residual limb dermal surface. Pistoning is the result of these axial movements between the liner and the socket that can grow local dermal abrasions and ultimately lesions. Embodiments of the present disclosure reduce such pistoning.

Often, lesions are seen at the proximal medial (i.e., inner groin) and distal lateral areas of the residual limb. High pressures transferred to the skin areas from the conventional socket to the liner may lead to shearing of epidermal cells on a microscopic level, and subsequently the generation of skin debris. Ultimately, this complex set of events at the skin surface can lead to abrasions and lesions because the local environment under the liner is a closed system and can lead to rapid growth of bacterial species. Another source of lesions occurs adjacent the distal lateral location where the mechanically unrestrained remaining portion of the femur can impact the internal surface of the remaining musculature. These internal impact forces are subsequently transferred through the skin and cause exterior lesions. Embodiments of the current disclosure mitigate such lesions.

Medical Adhesives

In some embodiments, a medical adhesive 34 is used as an anti-pistoning and anti-lesion material. The medical adhesive creates a temporary, or selectively detachable, bond or interface between the socket and the patient. During the stance phase of the gait cycle where compression force is prevalent (much of the patient's weight bears axially downward onto the bottom surface of the socket), the material may provide a cushioning effect to the residual limb and in particular, a compliant cushion at any irregular dermal features, such as scars, burns, or lesions. During the entire gait cycle, this material may act as a weak adhesive yet have sufficient strength to bond the electronics liner 24 directly to the residual limb 12 over multiple socket mounting and demounting cycles. In addition, the selected weak adhesive may reliably perform under a variety of loads, including tension, shear, torsion, and lateral loads, at the skin-liner bond line interface.

A medical adhesive 34 may be used to reduce pistoning and lesion formation. Referring now to FIG. 4, in some embodiments, a medical adhesive 34 may be configured for placement between the residual limb 12 and the electronics liner 24 and is effective to maintain a secure fit between the residual limb 12 and the electronics liner 24. In some embodiments, the medical adhesive 34 is a biomimetic material. In some embodiments, the medical adhesive 34 may be a hydrogel, a hydrocolloid, a hydrofoam, or a combination thereof. In some embodiments, the medical adhesive 34 may further include one or more secondary adhesives. In other embodiments, the medical adhesive 34 does not include a secondary adhesive.

In some embodiments, the medical adhesive 34 has the capability to wick wound exudates, thereby removing sources that stimulate bacterial growth at erosion or blister sites. The absorption of exudates may expedite wound healing and reduce the proliferation of bacteria along the skin surface.

Hydrogels

Hydrogels are a type of medical adhesive that may promote healing of wounds by removing exudates and ensuring a clean wound bed environment. Furthermore, hydrogels may act as desiccants that may prevent the formation of scar tissue. Also, hydrogels have excellent thermoconductivity properties that make them suitable for knee amputees wearing the prosthetic socket because hydrogels represent a low thermal impedance when removing heat from the residual limb. Specifically, hydrogels are cool on initial material application and are useful in thermal management when heating and cooling the residual limb.

In some embodiments, a commercial hydrogel wound dressing may be used as the medical adhesive 34. Hydrogels are network polymers that swell but do not dissolve in water. They are hydrophilic with high water retaining capability and high flexibility. In some embodiments, the hydrogel may be an amorphous hydrogel. Amorphous hydrogels lack the cross-linked polymer structure. Amorphous hydrogels can be manufactured in a tube form because these hydrogels lack a definite shape or amorphous hydrogels can be infused into gauze. In other embodiments, the hydrogel may be a fixed hydrogel. Fixed hydrogels are a network of cross-linked polymer chains. Fixed hydrogels are made into sheets or rolls. Also, because fixed hydrogels generally contain a defined cross-lined polymer chain, often this type of hydrogel contains a scrim. In some embodiments, the medical adhesive 34 may comprise both amorphous and fixed hydrogels. In other embodiments, the medical adhesive 34 may comprise either amorphous or fixed hydrogels.

In some embodiments, the medical adhesive 34 may comprise a hydrogel, a hydrocolloid, a hydrofoam, or a combination thereof. Hydrocolloids and hydrofoams are related to hydrogels. Hydrocolloid material (e.g., Kendall™ Aquaflo™ Hydrophilic wound dressings from Covidien, Mass., USA) creates a seal around the wound that may prevent the release of moisture that results from daily activities. Hydrocolloids do not contain water. Hydrocolloids are used more for pressure ulcers such as those seen in diabetic patients. Hydrofoams (e.g., Aquasorb® Hydrogel Wound Dressings from DeRoyal®, Indiana, USA) may be made of a hydrophilic polyurethane foam. The purpose of the foam is to absorb the excess exudate. Additionally, in some embodiments, a hydrocolloid hydrogel hybrid (Water Ltd.) may be used as a medical adhesive 34.

In other embodiments, other types of polymer gels, foams, and biomimetic nano surfaces, such as biomimetic gecko foot pad, are suitable for the anti-pistoning function and may be used as a medical adhesive 34.

In some embodiments, the medical adhesive 34 may be shaped as a square or rectangular patch, a sheet, a rope, and combinations thereof. In some embodiments, the medical adhesive 34 has a thickness in the range of about 0.025 inches to about 0.055 inches, about 0.015 inches to about 0.035 inches, about 0.010 inches to about 0.030 inches, or about 0.010 inches to about 0.020 inches thick.

Biocides

In some embodiments, the medical adhesive 34 further contains one or more biocides. Depending on the application, one or more biocides may be incorporated into the medical adhesive 34 before, during, or after the manufacturing process. In some embodiments, the medical adhesives 34 are compounded with silver particles, a natural biocide. In some embodiments, hydrogels are compounded with silver particles. The silver particles may provide a broad spectrum protection against common contact and airborne bacteria and promote rapid healing. The high thermal conductivity of silver (489 W/K·m, the highest of any metal) may also aid in cooling high temperature areas resulting from skin friction. If blisters, sores, or lesions are present on the residual limb 12 surface, the biocide may minimize any additional infections and promote healing. In some embodiments, polyethylene oxide may be used as the biocide.

Thermal Management

In some embodiments, a temperature control system is integrated into the electronics liner 24. The temperature control system may include components: (1) miniature thermal electric coolers (TECs) to inject or remove heat; (2) a flattened heat spreader to provide a thermal conduit; (3) a phase change material that may help maintain a constant temperature near the skin surface; and (4) a combination thereof.

Thermal Electric Coolers

Figure 5:
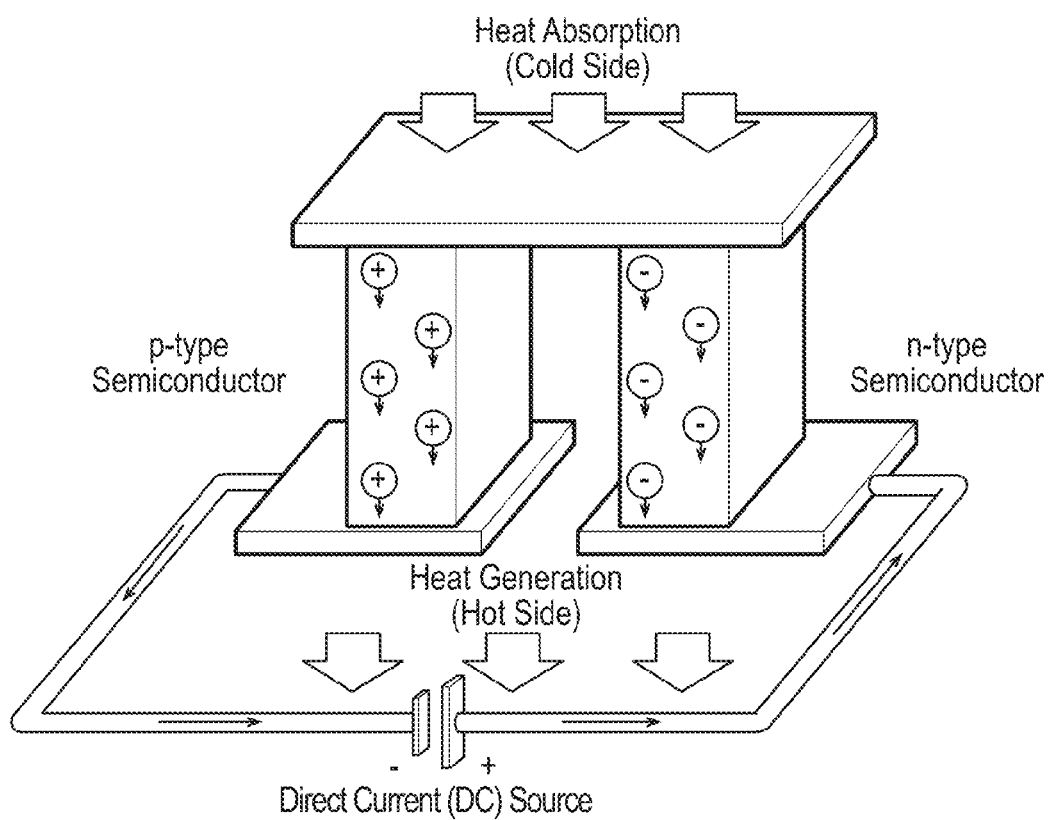
FIG. 5 is a schematic view of a thermal electric cooler made with two types of semiconductors, in accordance with embodiments of the present disclosure.

TECs are based on the Peltier effect. When electrical current flows through dissimilar junctions made of different metals or semiconductors of different types, heat flows from one side to the other and result in a cold and hot surface at opposite junctions. FIG. 5 shows a schematic of a TEC element made of two types of semiconductors (p-type and n-type) and its working principles. A direct current flows from p-type to n-type semiconductors and produces cold and hot surfaces. The surface identities (cold or hot) may be reversed by reversing the direction of current flow. Under the configuration shown in FIG. 5, heat is absorbed at the top and released at the bottom. By changing the polarity of the applied DC current, the TEC can be made to alternate heat flow from one side of the device to the other, enabling on-demand cooling or heating.

In some embodiments, the electronics liner 24 includes a TEC positioned for contact with the residual limb 12, a heat spreader, a phase change material 32, or a combination thereof. The TECs respond to temperature changes of the residual limb 12 in a manner that is effective to maintain a desired temperature within the electronics liner 24. In some embodiments, the desired temperature within the electronics liner 24 is normal body temperature. In some embodiments, the TECs respond to temperature changes in a manner that is effective to maintain an inner surface area 28 of the electronics liner 24 at a temperature that is plus or minus 10° F., plus or minus 5° F., or plus or minus 2° F. of normal body temperature.

In some embodiments, the electronics liner 24 may include one or more miniature TEC devices. The TEC may be obtained from a commercial source or custom made. In some embodiments, the TECs are about 2 mm thick and about 25 mm long with two wire leads. In embodiments, an array of these devices is placed within the electronics liner 24 distributed on a power bus matrix. Depending on the performance of the control loop for the cooling system and patient's comfort needs, the TEC devices may be configured into two or more zones within the device, each having its own controller, temperature sensor, and/or temperature setting. Given that only a few degrees Fahrenheit temperature differentials relative to the skin is required for comfort, in some embodiments this light demand allows the TECs to be activated only intermittently using a closed loop thermal management program within an onboard microprocessor package. In some embodiments, each TEC device has a corresponding temperature sensor mounted adjacent to it. Their placement and working mode may be optimized through numerical modeling.

Heat Spreaders

In some embodiments, the electronics liner 24 includes a heat spreader positioned for contact with the residual limb 12, TECs, a phase change material, or a combination thereof. The heat spreader responds to temperature changes of the residual limb 12 and the prosthetic socket 20 in a manner that is effective to maintain a desired temperature within the electronics liner 24. In some embodiments, the heat spreader responds to temperature changes in a manner that is effective to maintain an inner surface area of the electronics liner 24 at a temperature that is plus or minus 10° F., plus or minus 5° F., or plus or minus 2° F. of normal body temperature.

Low thermal impedance heat spreaders may be used in certain embodiments to physically connect the TECs to phase change material (detailed below) pads that may be in contact with the medical adhesives 34, adjacent to the residual limb 12 skin. In other embodiments, the heat spreader may also be used on the other side of the TECs to evenly distribute the heat toward the foam layer 16. In certain embodiments, the heat accumulation on the side of the exterior surface of the electronics liner 23 away from the residual limb 12 is low and active removal of heat may not be required.

In some embodiments, the heat spreader may include buckypapers. Buckypapers are made of carbon nanotubes, which have the highest thermal conductivity among most materials at a fraction of the weight. In certain embodiments, the thermal conductivity can be further enhanced by alignment of the carbon nanotubes (CNTs) in buckypapers, where most of the CNTs are oriented in the direction of the desired heat flow. In some embodiments, the buckypapers have a thermal conductivity of greater than about 100 W/(K m), in the range of about 50 to 100 W/(K m), or in the range of about 75-100 W/(K m).

Phase Change Materials

Phase change materials (PCMs) are substances that undergo the process of changing phases, such as from solid to liquid or vice versa. These changes are accompanied by energy absorption (from solid to liquid, or melting) or release (from liquid to solid, or solidification), thereby providing a mechanism for removing or injecting heat. Some PCMs change phases within a temperature range that is just above and below human skin temperature.

In some embodiments, the electronics liner 24 includes a PCM 32 positioned for contact with the residual limb 12. The phase change material 32 responds to the temperature changes of the residual limb 12 in a manner that is effective to maintain an inner surface area of the electronics liner at a temperature that is plus or minus 10° F., plus or minus 5° F., or plus or minus 2° F. of normal body temperature.

In some embodiments, the PCMs 32 are encapsulated PCMs 32, for example a solid-liquid PCM 32 core imbedded within silicon rubber. In some embodiments, the PCMs 32 are solid-solid PCMs 32 which may be flexible in the solid state. In still other embodiments, the PCMs 32 are solid-liquid PCMs 32. In some embodiments, PCMs 32 in the form of microcapsules are incorporated within fibers or foams. In some embodiments, PCMs 32 in the form of microcapsules are coated onto fabrics. The microencapsulation may enable larger surface contact areas and more efficient heat exchanges. Applying the PCM 32 as coatings may also help to maintain the air permeability of the textiles.

In some embodiments, the PCMs 32 are placed on the inner surface 28 of the electronics liner 24 underneath a medical adhesive layer 34, and can interface with the low thermal impedance heat spreaders. When heat is generated at the limb surface rises, the PCM 32 may start to melt to absorb the heat and provide cooling. In some embodiments, once the PCM 32 is liquefied, the thermal management system may initiate the TEC modules to provide cooling across the lower thermal impedance heat spreaders and into the PCMs 32. This may start the cooling of the limb by regenerating a solid PCM 32 for melting. In some embodiments, the cooling duration provided by the TEC is controlled by a closed loop system to provide the requisite cooling effect minimizing demand on battery capacity.

In still other embodiments, the working modes of PCMs 32 (solidifying instead of melting) and TECs (heating instead of cooling) are reversed and the residual limb 12 is instead heated. Since the PCMs 32 may be in close proximity to the residual limb 12 surface, the latency of temperature thermal cycles may be low. This may allow rapid heating or cooling of the residual limb 12 as needed to maximize patient comfort.

The energy absorbing/releasing capacity of a PCM 32 is exhausted once the phase change is completed. In some embodiments, the capacity is regenerated by re-solidification or re-melting with the assistance of an external energy source, for example the TEC in the thermal management system. By controlling the melting and solidification processes through removing or injecting heat with the TECs, these PCMs 32 may be able to maintain a constant temperature.

Integrated Electronics

Turning now to FIG. 4, the prosthetic sock may also include an electronics liner 24 that is configured for placement between the residual limb 12 and the inner layer 14 of the prosthetic sock 10. The residual limb 12, the electronics liner 24, and the prosthetic sock 10 may then be fitted into a prosthetic socket 20. The prosthetic socket 20 shell may be fabricated from carbon fiber reinforced polymer resin composites using commercially available fabrication methods, such as resin transfer molding.

Integrated Sensors

The inner surface 28 of the electronics liner 24 may comprise one or more integrated sensors 26 that are located across areas of the inner surface 28. These sensors 26 are positioned for contact with the residual limb 12. In some instances, the contact with the residual limb 12 is direct sensor-to-limb contact. In other instances, contact with the residual limb 12 is the contact with a thin material or space between the residual limb 12 and the sensor 26. The contact with the limb 12 is effective for the particular type of sensor 26 used.

The integrated sensors 26 include, but are not limited to, sensors for monitoring pressure, temperature, moisture, odors, and acceleration. In some embodiments, an accelerometer is used to detect movement and positions/orientations. In embodiments, an electronic odor sensor measures changes in the limb cavity caused by moisture and pressure to various sections in sections of the limb during use. This sensor may monitor the state of the residual limb 12 in the socket 20 and the sensitivity of the residual limb 12 to react to small changes that makes the wearing of the electronics liner 24 uncomfortable. In some embodiments, sensing (sniffing) body spoilage rate monitoring may be done by examining color changes in a sensor scanned by a mini camera that can notice changing color patterns that correspond to chemical changes.

Piezoelectric Sensors

Figure 6:
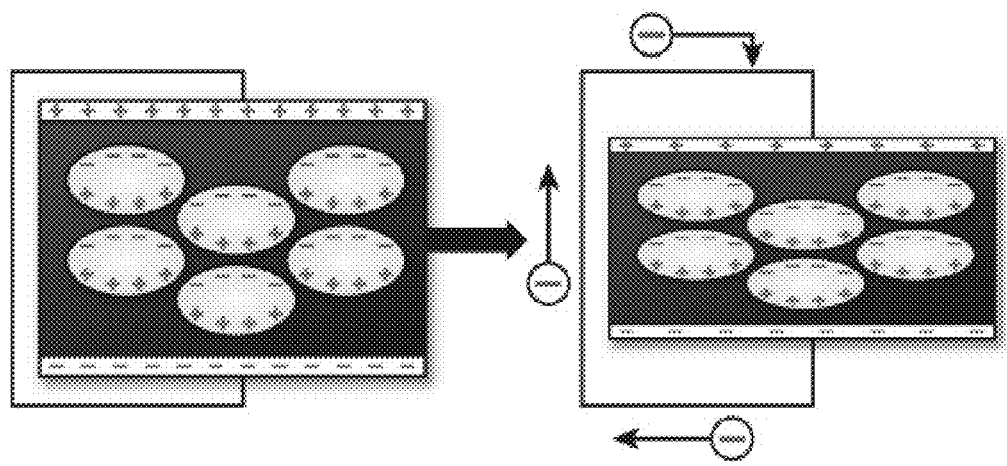
FIG. 6 is a schematic view of a piezoelectric foam for pressure sensing, in accordance with embodiments of the present disclosure.

Piezoelectric foams (ferroelectrics) are space-charged electrics made from polymer foams that show strong piezoelectric activity, resulting from the macroscopic dipoles residing in their pores. Their piezoelectric activities rival those of the best ceramic based materials. They also possess many advantages over their inorganic counterparts, such as being thin, lightweight, flexible, low-cost, non-toxic and easy to process. FIG. 6 shows the basic working principle of these materials. The deformation of charged pores under stress results in a change in the macroscopic dipole, leading to an external electric signal (sensing signal). Conversely, an applied external field results in deformation of the pores and materials displacement (actuation).

In some embodiments, the integrated sensors 26 are piezoelectric sensors. In some embodiments, the integrated sensors 26 are piezoelectric foam sensors. The piezoelectric foam pressure sensor transforms pressure signals into electrical signals. These sensors may be incorporated into the electronics liner 24 to measure the 3D whole-field pressure distribution at the limb-liner interface in real-time to achieve several functions. They may be used to ensure proper limb-socket interface contact. These pressure sensors may also be used to monitor pressure changes throughout the gait cycle, e.g., when and where the pressure changes take place. In certain embodiments, an onboard alarm system may alert the patient of potential adverse situations when elevated pressures occur.

In still other embodiments, pressure sensing is accomplished using pressure sensors 26 that do not comprise a piezoelectric material.

Data Analysis and Patient Feedback

The integrated sensors 26 may be in communication with one or more devices located on the inner surface 28 or the outer surface of the electronics liner 24. In some embodiments, the inner surface may include temperature regulation devices 30 that are in communication with an integrated sensor 26, for instance a temperature sensor. In some embodiments, perspiration control is monitored by the responses to changes in temperature. In certain embodiments, feedback control circuits are fabricated to link the pressure sensors at the limb/liner interface and volume management materials to provide an active actuation mechanism.

Electrical circuits throughout the electronics liner 24 allow data collection, storage, and wireless transmission. In some embodiments, the sensors 26 or devices are partially or fully embedded in the electronics liner 24. In some embodiments, the sensors 26 are printed electronic sensors, for instance temperature and moisture sensors, and are fully embedded in the electronics liner 24. As used herein, the term "integrated" means that the device or sensor is located either on the inner surface 28 of the electronics liner 24 or is embedded in the electronics liner 24.

Additional electronic modules may be located on the outer surface of the electronics liner 24 and may be connected to devices and sensors located on the inner surface 28 or the outer surface of the electronics liner 24. In some embodiments, the outer surface of the prosthetic socket 20 includes an electronics compartment 36 that comprises plastic receptacles for the simple removal and replacement of electronic modules. In some embodiments, electronic modules are designed and manufactured as "slide-in" modules to support the proper functioning of the environmental elements (including but not limited to TECs, temperature and moisture, and pressure sensors), and real-time data collection, storage, and wireless transmission. In some embodiments, a lightweight, compact data collection system is used to continuously collect and record data.

In embodiments, sensor data is simultaneously digitized and processed with time stamps to track the sensors, real time data, and changes. In some embodiments, each sensor type is sampled at its assigned rate and all the sensor types operate simultaneously under sampled sensor controls. In certain embodiments, each pressure sensor requires a voltage follower amplifier so multiple sensors may feed into a programmable multi-channel analog to digital converter ("ADC") with self-contained multiplex controls in a specified sequence and gain settings before digitalization of each channel specified for that sector location. In other embodiments, temperature sensors require a less complex ADC device with its onboard temperature sensors so differential computations can be measured instead of needing a highly accurate array of sensors. In certain embodiments, ADCs of 4 to 16 channels per device are used to reduce the number of devices required to cover all the sensors. In certain embodiments, all of the ADCs are linked to synchronize the sensors, although the sample rates may be different.

In embodiments, the integrated electronic devices, sensors, and modules work together to perform any array of functions, including regulating power for the sensors, the computational and signal processing functions embedded in the DSP, the closed loop control of a thermoelectric cooler array, the adaptive control systems, the data storage system, a wireless link for external laptop communications, an alarm messages function, or combinations thereof. In some embodiments, the integrated electronics accepts many types of sensors, digitizes each sensor, and processes each type of sensor to perform real time adaptive control. In some embodiments, the integrated electronics are configured to glean intelligence information in real time for user information. In certain embodiments, the integrated electronics is configured to store sensor data for later analysis regarding performance and comfort. In some embodiments, this system includes retrieval on command via wired or wireless communications of stored data, storage of critical sensor and processed information in a removable SD microchip, wireless response to commands issued from a laptop computer, the tailoring of sensor responses to individual user needs, acceptance of adaptive changes to monitoring operations to extend user comfort over usage time, and combinations thereof.

A function of the signal processing is to provide meaningful sensor information to the patient so that he may react to and correct for changes in pressure, temperature, and other dynamic socket variations. The sensors may provide the patient with an early warning of adverse situations, such as abnormal pressure suggesting improper gait or pistoning, and allow the patient to make needed adjustments. In other embodiments, the signal processing provides sensor information to an automated system so that, for instance, an automated adaptive control system can react to and correct for changes in pressure, temperature, and other dynamic socket variations.

An onboard alarm subsystem may alert the patient of potential adverse situations when elevated pressures are present. In some embodiments, the subsystem includes embedded, distributed temperature sensors for sweat control with a TEC array embedded in the socket 20. A lightweight, compact data collection system may continuously collect and record data. Wireless data transfer and storage is accomplished using RFID and flash memory technologies. These data can be utilized by the health care practitioner to analyze the patient conditions and track their rehab progress.

It should be apparent that the foregoing relates only to the preferred embodiments of the present invention and that numerous changes and modifications may be made herein without departing from the spirit and the scope of the invention as defined by the following claims and equivalents thereof.

We claim:

1. A prosthetic sock for a patient to wear over a residual limb, the prosthetic sock comprising:
    an inner layer configured to fit over at least a portion of the residual limb;
    a foam layer disposed on an outer surface of the inner layer and configured to maintain a secure fit between the residual limb and a prosthetic socket via shape change in response to changes in shape or volume of the residual limb within the prosthetic sock, wherein the foam layer comprises an auxetic foam; and
    an electronics liner, which, when the prosthetic sock is worn, is located between the residual limb and the inner layer,
    wherein the electronics liner comprises
        (i) a phase change material which is encapsulated or is imbedded within the electronics liner and is configured to absorb heat from the residual limb by undergoing a solid-to-solid or solid-to-liquid phase change effective to maintain an inner surface of the electronics liner at a selected constant temperature that is within 10° F. of normal body temperature,
        (ii) one or more thermal electric coolers disposed on the inner surface of the electronics liner and configured to cool and regenerate the phase change material, wherein the one or more thermal electric coolers have a cold surface and a hot surface, and
        (iii) one or more low thermal impedance heat spreaders positioned to physically connect the cold surface of the one or more thermal electric coolers to the phase change material.

2. The prosthetic sock of claim 1, wherein the foam layer is configured to change shape to substantially match a shape of the residual limb.

3. The prosthetic sock of claim 1, further comprising an outer layer located along an outer surface of the foam layer.

4. The prosthetic sock of claim 1, wherein the foam layer has an initial volume and the foam layer is configured to change to a second volume that is from about −100% to about 300% of the initial volume.

5. The prosthetic sock of claim 1, further comprising:
    one or more integrated sensors located across at least a portion of the inner surface of the electronics liner and positioned for contacting the residual limb.

6. The prosthetic sock of claim 5, wherein the one or more thermal electric coolers are in communication with the one or more integrated sensors.

7. The prosthetic sock of claim 1, comprising a dermal adhesive configured for placement between the residual limb and the electronics liner and effective to maintain a secure fit between the residual limb and the electronics liner.

8. The prosthetic sock of claim 1, further comprising one or more heat spreaders positioned to evenly distribute heat from the one or more thermal electric coolers toward the foam layer.

9. The prosthetic sock of claim 1, wherein the one or more heat spreaders comprise a buckypaper.

10. A system for securing a residual limb in a prosthetic socket of a prosthetic limb, the system comprising:
   a prosthetic sock to be worn over the residual limb of a patient, wherein the prosthetic sock comprises an inner layer and a foam layer which comprises an auxetic foam; and
   an electronics liner, which, when the prosthetic sock is worn, is located between the residual limb and the inner layer, wherein the electronics liner comprises
      (i) a phase change material which is encapsulated or is imbedded within the electronics liner and is configured to absorb heat from the residual limb by undergoing a solid-to-solid or solid-to-liquid phase change effective to maintain an inner surface of the electronics liner at a selected constant temperature that is within 10° F. of normal body temperature,
      (ii) one or more thermal electric coolers disposed on the inner surface of the electronics liner and configured to cool and regenerate the phase change material, wherein the one or more thermal electric coolers have a cold surface and a hot surface, and
      (iii) one or more low thermal impedance heat spreaders positioned to physically connect the cold surface of the one or more thermal electric coolers to the phase change material,
   wherein the prosthetic socket is configured to receive the residual limb with the prosthetic sock thereon, and
   wherein the prosthetic sock compensates for shape or volume changes in the residual limb by changing shape to maintain a secure fit between the residual limb and the prosthetic socket.

11. The system of claim 10, wherein the foam layer is disposed on an outer surface of the inner layer and responds to changes in shape or volume of the residual limb disposed within the prosthetic sock by changing shape in a manner effective to maintain a secure fit of the prosthetic socket.

12. The system of claim 11, further comprising one or more heat spreaders positioned to evenly distribute heat from the one or more thermal electric coolers toward the foam layer.

13. The system of claim 10, wherein the electronics liner comprises one or more integrated sensors positioned for contacting the residual limb.

14. The system of claim 10, wherein the one or more heat spreaders comprise a buckypaper.

15. A system for managing a prosthetic limb worn by a patient, the system comprising:
   an electronics liner for disposition over a residual limb of the patient, wherein the electronics liner comprises
      (i) a phase change material which is encapsulated or is imbedded within the electronics liner and is configured to absorb heat from the residual limb by undergoing a solid-to-solid or solid-to-liquid phase change effective to maintain an inner surface of the electronics liner at a selected constant temperature that is within 10° F. of normal body temperature,
      (ii) one or more thermal electric coolers disposed on the inner surface of the electronics liner and configured to cool and regenerate the phase change material, wherein the one or more thermal electric coolers have a cold surface and a hot surface, and
      (iii) one or more low thermal impedance heat spreaders positioned to physically connect the cold surface of the one or more thermal electric coolers to the phase change material;
   a prosthetic sock, having a foam layer that comprises an auxetic foam, to be worn over the electronics liner and the residual limb, wherein the prosthetic sock is configured to change shape in a manner effective to maintain a secure fit of the residual limb in a prosthetic socket of the prosthetic limb in which the foam layer changes shape in response to a change in shape or volume of the residual limb; and
   the prosthetic socket for receiving the prosthetic sock, the electronics liner, and the residual limb.

16. The system of claim 15, wherein the electronics liner comprises one or more integrated sensors positioned for contacting the residual limb.

17. The system of claim 16, wherein the one or more thermal electric coolers are in communication with the one or more integrated sensors.

18. The system of claim 17, further comprising a dermal adhesive configured for placement between the residual limb and the electronics liner and effective to maintain a secure fit between the residual limb and the electronics liner.

19. The system of claim 15, further comprising one or more heat spreaders positioned to evenly distribute heat from the one or more thermal electric coolers toward the foam layer.

20. The system of claim 15, wherein the one or more heat spreaders comprise a buckypaper.

* * * * *